United States Patent

Goloschapov et al.

[11] 4,151,281
[45] Apr. 24, 1979

[54] MEDICINAL PREPARATION FOR THE TREATMENT OF COLLAGENOSES OF A RHEUMATOID NATURE

[76] Inventors: Nikolai M. Goloschapov, ulitsa Druzhby, 9, kv. 110, Zagorsk Moskovskoi oblasti; Yakov A. Sigidin, Kutuzovsky prospekt, 5/3, korpus 2, kv. 132; Elena S. Tsvetkova, ulitsa Novatorov, 20, korpus 1, kv. 119, both of Moscow; Ida L. Bilich, ulitsa Nikolaya Ershova, 55, kv. 24, Kazan; Vladimir S. Reznik, ulitsa Gospitalnaya, 34, kv. 34, Kazan; Nikolai G. Pashkurov, ulitsa Druzhby, 6, kv. 20, Kazan; Galina F. Zaika, ulitsa Druzhby, 9, kv. 110, Zagorsk Moskovskoi oblasti; Abdurakhim A. Muslinkin, ulitsa Zhdanova, 60, kv. 33, Kazan, all of U.S.S.R.

[21] Appl. No.: 843,818

[22] Filed: Oct. 20, 1977

[51] Int. Cl.² .................. A61K 31/505; C07D 239/00
[52] U.S. Cl. ...................................... 424/251; 544/296
[58] Field of Search ....................... 424/251; 260/256.5

Primary Examiner—Stanley J. Friedman
Attorney, Agent, or Firm—Lackenbach, Lilling & Siegel

[57] ABSTRACT

A medical preparation for the treatment of collagenoses of a rheumatoid nature, comprising, as the active principle, p,p-/2,4-dioxy-6-methyl-pyrimidinyl-5-sulfoamino/diphenyl sulfone with the following formula:

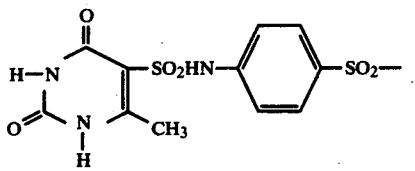

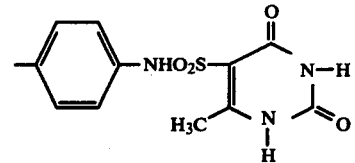

and a suitable pharmaceutical filler.

The preparation is used for the treatment of various collagenoses of rheumatoid nature, such as rheumatoid arthritis, systemic scleroderma, systemic lupus erythematosus, and others. The preparation is of low toxicity and does not produce side effects.

5 Claims, No Drawings

MEDICINAL PREPARATION FOR THE TREATMENT OF COLLAGENOSES OF A RHEUMATOID NATURE

The present invention relates to medicine, specifically to a new preparation for the treatment of collagenoses of a rheumatoid nature.

The new medicinal preparation for the treatment of collagenoses of a rheumatoid nature comprises, according to the invention, as the active principle p,p-2,4-dioxy-6-methyl pyrimidinyl-5-sulfonamide/diphenyl sulfone with the following formula:

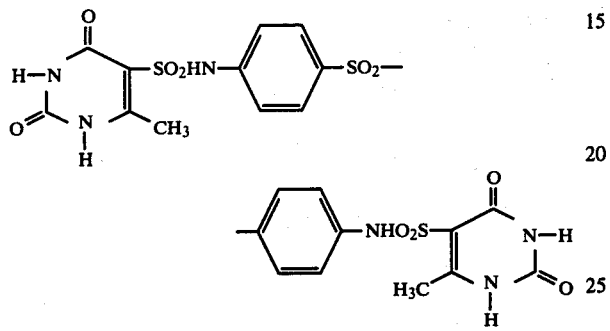

in combination with a pharmaceutical carrier.

The proposed medicinal preparation finds application in the treatment of various forms of collagenoses of rheumatoid nature, such as, for example, rheumatoid arthritis, systemic scleroderma, systemic lupus erythematosus, and others.

The proposed preparation was tested for toxicity in the acute and chronic tests. The acute toxicity of the preparation was determined in tests in albino mice (weighing 16 to 17 g) by introducing (by means of a probe into the stomach) amounts equal to 1,000 to 5,000 mg/kg of the animals body weight. Each dose was tested in five animals. Observation was continued for three days. It was established that the $LD_{50}$ according to Litchfield and Wilcoxson is 2,600 (2,136 to 3.042) mg/kg.

It has been established that, in the case of a single administration (by means of a probe into the stomach) of a 100 to 200 mg/kg dose to narcotized cats weighing 2 to 3 kg, the preparation causes no visible changes in the animals. In 10 to 20 minutes after the administration of a 500 mg/kg dose of the preparation, unrest is observed (motorial excitation, mewing, salivation and vomiting). After a 1,000 mg/kg dose, these symptoms are more pronounced. There is repeated vomiting and loss of appetite (during the first 24 hours, the animals touched neither milk nor meat); on the second day after the administration of the preparation, the animals' condition returned to normal.

When studying the toxicity of the preparation in the chronic test, white rats weighing 160 to 180 g were given daily 500 mg/kg and 1,000 mg/kg bodyweight doses for three months. Each dose was investigated in 20 animals (10 males and 10 females). Twenty rats served as controls. Changes in weight were recorded, the general status and behavior were observed, the peripheral blood picture was examined (hemoglobin, erythrocytes, leukocytes, thrombocytes, the leukocytary formula). For determining the functional state of the liver, kidneys, the pancreas, some biochemical indices of the urine (albumin, sugar, bile pigments) and the blood (sugar, cholesterol, bilirubin, urea, alkaline phosphatase, chlorides) were examined, just as the antitoxic function of the liver.

After the end of the tests the animals were slaughtered by decapitation: part of them immediately after the administration of the preparation, part-ten days later.

The internal organs of the slaughtered animals were examined both macro- and microscopically.

Observations revealed that the proposed preparation does not cause any substantial changes in rats given 500 mg/kg and 1,000 mg/kg bodyweight doses in chronic tests. As to putting on weight, there was no difference between the test and the control rats (average weight increment: 50 to 70 g). Administration of the above mentioned doses caused no changes in the peripheral blood picture or the chemical indices of the urine and blood, as indicated by the data shown in the Tables No. 1 and No. 2.

Table 1

Effect of Preparation on Peripheral Blood Picture

| Dose of preparation, mg/kg | Before administration | | | After 3 months of administration | | |
|---|---|---|---|---|---|---|
| | Hemoglobin, g% | Erythrocyte, mln | Leukocytes, thou. | Hemoglobin, g% | Erythrocytes, mln | Leukocytes, thou. |
| 500 | 15.9 | 4.7 | 11.2 | 16.2 | 4.8 | 10.8 |
| 1,000 | 16.0 | 4.8 | 12.0 | 16.4 | 4.8 | 12.0 |

Table 2

Effect of Preparation on the Concentration of Sugar, Cholsterol, Urea, Chlorides in the Blood, on the Anti-Toxic Function of the Liver and the Activity Alkaline Phosphatase $P = 0.05$

| Biochemical indices | Controls | | After 3 months of administration of 100 mg/kg oral doses | |
|---|---|---|---|---|
| | females | males | females | males |
| Sugar mg % | 96±0.8 | 94±1.2 | 92±0.7 | 90±0.8 |
| Cholesterol mg% | 67±2.7 | 68±4.65 | 68±3.2 | 69±2.1 |
| Urea mg% | 34±0.5 | 32±2.75 | 32±2.3 | 38±2.1 |
| Chlorides mg% | 648±1.35 | 638±6.44 | 637±3.2 | 638±5.8 |
| Activity of alkaline phosphatase | 1.0±0.1 | 0.9±0.2 | 1.2±0.06 | 0.8±0.14 |
| Index of antitoxic function of the liver (quantity of isolated benzoic acid) | 10.1±5.1 | 6.68±0.33 | 10.9±2.2 | 6.5±1.14 |

Post mortem examination established that the animals were of good fattiness. The weight of the thyroid gland, testes, the spleen and adrenal glands of the animals did not differ from the weight of these organs in the control group animals.

Macro- and microscopic examination of the brain, heart, liver, spleen, kidneys, adrenal glands, stomach, intestine, ovaries, testes, bone marrow, pancreas, thyroid gand revealed no pathological changes.

A 48-hour study of the effect of the preparation on cell growth in a culture of normal fibroblasts taken from healthy donors demonstrated that the presence of the preparation in 100-gamma per 1 ml of medium results in a 30% reduction of the number of cells in the culture. This fact explains to a certain degree the action mechanism of the preparation in cases of systemic scleroderma.

Accordingly, the observed increase of the concentration of corticosteroids in the blood of rheumatoid arthritis or systemic lupus erythematosus patients, regularly given the proposed preparation during clinical trials in the above mentioned doses, testifies to its stimulating effect on the andrenal cortex.

The proposed preparation has been clinically tested.

The method of treatment consists in oral administration of the proposed preparation in 0.1 to 0.2 g doses in tablet form three to four times a day, or in the form of a 5% solution for injections with 5 ml doses once a day. The daily dose shall not be over 0.6 g per patient.

The main group (69 persons) consisted of patients with rheumatoid arthritis in the 2nd and 3rd degree of activity.

The first manifestations of the preparation's effect in cases of rheumatoid arthritis, observed after two days, consist in the abatement of the severity and duration of morning-time torpidity and in greater scope of movement by the affected joints. This effect was registered in 59 out of the 69 patients. Further on, morning-time torpidity disappeared completely in 48 patients. In the other patients, the period of morning-time torpidity shortened from $103.3 \pm 14.4$ min to $41.4 \pm 9.73$ minutes. The pain syndrome tangibly abated towards the end of the first week of treatment and in the majority of patients (51) it disappeared on the 10th to 12th day, nor did it return while the administration of the preparation was continued. The other 18 patients had only an abatement of the pain syndrome (arthralgia).

The articular index reduced during the period of treatment in 61 patients from 46-48 points to 16-20 points on an average, remaining without change in 8 patients only.

The first compression force increased in all the patients from $14.4 \pm 1.7$ kgf to $22.0 \pm 2.1$ kgf on an average.

Eight of the gravest patients, three of whom were bed-ridden for 3 to 5 years, following administration of the preparation for 1.5 to 2 years, became capable of taking care of themselves unaided, and no longer went into the hospital in spring and autumn. Moreover, six of them are managing on essentially reduced doses of corticosteroids, and two patients do not need them any more at all.

As treatment with the preparation continued, a reduction in the ESR and of the sialic acid content of the blood was observed in most of the patients (by 0.05 optical density units) and of C-reactive protein from (+ + + +) to (+ +) and even (+), as well as an increase in the corticosteroid content in the blood due to the increasing activity of the 11-oxicorticosteroids. Patients in whom rheumatoid arthritis was accompanied by leukopenias or leukocytoses showed a tendency towards the normalization of the leukocyte count.

Improvement of these therapeutic indices began, as a rule, not later than 3 to 4 weeks after the beginning of treatment and only in 8 patients such improvement took much longer.

Eight patients were treated for systemic lupus erythematosus. Complete recovery was observed in one case, when following the intake of the preparation for two years this patient fully regained working capacity for two months in a row in spring and autumn. In the other cases, the administration of the proposed preparation makes it possible to substantially alleviate the complications due to the use of corticosteroids and quinoline preparations.

Five patients were treated for systemic scleroderma. All of them manifested a reduction of skin induration, of the flexion contracture of the hand and subjective sensation of skin tension. One of these patients, following a 1.5 year course of treatment, resumed work after a three-year interval caused by the disease.

The above results are not produced when systemic scleroderms is treated with preparations of the type of Brufen, Indometacin, corticosteroids, quinoline derivatives and other preparations known in the art.

By its action, the proposed preparation differs from a number of medicinal remedies used in the therapy of collagenoses of a rheumatoid nature.

Thus, for example, antimalarial preparations used for the treatment of collagenoses of a rheumatoid nature (Delagil, Resoquine, Chloroquine, Tanakan, Avlochlor, Arfrochin) cause leukopenia, and also affect the acoustic and optic nerves, the liver, the myocardium, etc., and for this reason cannot be used for lasting treatment. The proposed preparation has low toxicity and its lasting administration (1-2 years and more) does not cause the above-mentioned complications.

The proposed preparation differs from the derivatives of indole (Indometacin, Indacid, Inteban), which possess an ulcerogenic effect, i.e. cause the ulceration of the stomach, esophagus, the intestine, as well as cause mental disorders: confused consciousness, somnolency, in that it does not cause such complications even when used for many years. On the contrary, the presence of two pyrimidine bases in its composition may help in stimulating processes of regeneration.

The preparation differs from glucocorticosteroids (cortisone, hydrocortisone, prednisone, prednisolone, dexamethazone, triamcinalone, and others), which increase the excretion of the salts of potassium and calcium from the organism and the retention of the salts of sodium and of water, which induces the appearance of edemas, raises blood pressure and the sugar content of the blood (steroid diabetes), exacerbate gastric ulcer, reduce the organism's resistance to infection, and during lasting administration may cause strophy of the adrenal cortex, in that it stimulates the function of the adrenal cortex, as testified by the rising corticosteroids content of the blood during treatment with this preparation. Besides, the preparation does not cause general and water-and-salt metabolic disorders, but, on the contrary, when present, these disorders tend to normalize, thus permitting the dosage of prescribed corticosteroids to be reduced and, in individual cases, discontinuing them altogether.

The active principle of the proposed preparation, p,p-/2,4-dioxy-6-methyl pyrimidinyl-5-sulfonamino/-diphenyl sulfone can be produced in the following way.

6-methyluracil is made to interact with chlorosulfonic acid. When doing this, in order to avoid local overheating and to reduce the adhesion of 6-methyluracil into lumps and its build-up on the walls of the reaction vessel, the chlorosulfonic acid should be distributed as evenly as possible and a temperature not higher than 50° C. should be maintained.

Thionyl chloride is poured into the obtained mass while cooling and the reaction mixture is then heated up to 70° C., and further to 75°-78° C., then kept within this temperature range for 8 hours, after which it is cooled to 20°-25° C.

The obtained mass is poured in a thin trickle onto finely crushed ice. The yellowish precipitate of 5-sulfochloride-6-methyluracil, that falls out in the process, is filtered off, washed with chilled water and chilled acetone and dried under vacuum for 5 to 6 hours at a temperature not above 40° C.

Then, small portions of the 5-sulfochloride-6-methyluracil are introduced in powder form into a prepared solution of diaminodiphenyl sulfone in dry dimethyl formamide with the addition of triethanolamine. By the end of the introduction of the 5-sulfochloride-6-methyluracil, the temperature of this mixture must not exceed 60° C.

After keeping this mixture for an hour at a temperature of 50° to 60° C., it is cooled to 20°-25° C. and allowed to stay overnight, after which it is mixed with chloroform, the precipitated yellowish p,p-/2,4-dioxy-6-methyl pyrimidinyl-5-sulfonamino/diphenyl sulfone is filtered off and washed with chloroform and acetone. Ethanol is added to the washed p,p-/2,4-dioxy-6-methyl pyrimidinyl-5-sulfonamino/diphenyl sulfone, the mixture is heated to a temperature of 50° to 60° C., filtered once again, and the precipitate is air-dried.

The proposed preparation can be used in the form of capsules, tablets and solutions for subcutaneous or intramuscular injections. It is advisable to use starch as the pharmaceutical filler for tablets, with the active principle content in the tablets being 0.1 to 0.2 g per tablet.

It is preferable to use apyrogenic distilled water or a physiological salt solution as the solvent for injections.

Solutions for injections are used with a concentration of the active principle of 5 wt.%.

A single dose of the proposed preparation is 0.1 to 0.2 g; the daily dose is 0.6 g. The maximum daily dose is 1.0 g. When administered in tablet form, 0.2 to 0.1 g is given 3 to 4 times a day.

When administered as injections, it is, as a rule given, once a day in a 5 ml dose of a 5% solution.

The only contraindication to the use of the preparation is individual intolerance.

What is claimed is:

1. A medicinal preparation for the treatment of collagenoses of a rheumatoid nature, comprising, as the active principle, a medicinally effective amount of p,p-/2,4-dioxy-6-methyl-pyrimidinyl-5-sulfonamino/diphenyl sulfone with the following formula:

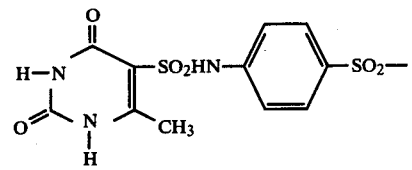

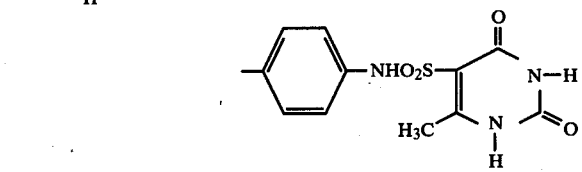

and a pharmaceutical carrier for said active principle.

2. A medicinal preparation as claimed in claim 1, comprising starch as the pharmaceutical carrier, serving as a filler for tablets.

3. A medicinal preparation as claimed in claim 2, comprising 0.1 to 0.2 g of said active principle per tablet.

4. A medicinal preparation as claimed in claim 1, in which said pharmaceutical carrier is a solvent selected from the group consisting of apyrogenic distilled water and a physiological salt solution.

5. A medicinal preparation as claimed in claim 4, comprising 5 wt.% of said active principle.

* * * * *